US005502247A

United States Patent [19]
Bartos et al.

[11] Patent Number: 5,502,247
[45] Date of Patent: Mar. 26, 1996

[54] PROCESS FOR RECOVERY OF AROMATIC ACID OR ESTER AND POLYOL FROM WASTE POLYESTER RESINS

[75] Inventors: Thomas M. Bartos, Naperville; Bruce I. Rosen, Morton Grove; Jeffrey I. Rosenfeld, Schaumburg, all of Ill.

[73] Assignee: Amoco Corporation, Chicago, Ill.

[21] Appl. No.: 341,012

[22] Filed: Nov. 17, 1994

[51] Int. Cl.$^6$ .......................... C07C 51/43; C07C 51/493
[52] U.S. Cl. .................................................. 562/486
[58] Field of Search ...................... 562/485, 486

[56] References Cited

U.S. PATENT DOCUMENTS

| | | | |
|---|---|---|---|
| 3,931,305 | 1/1976 | Fisher | 260/525 |
| 5,414,113 | 5/1995 | Broeker et al. | 562/413 |

*Primary Examiner*—JoséG. Dees
*Assistant Examiner*—Samuel Barts
*Attorney, Agent, or Firm*—Thomas E. Nemo; Wallace L. Oliver

[57] ABSTRACT

Processes are disclosed for recovery and purification of dibasic aromatic acids or esters thereof from waste polyester film, fiber, bottles, manufacturing residues, and other manufactured articles. The processes comprise: depolymerization of polyester resin in a liquid solvent under conditions of elevated temperature and pressure suitable for opening of ester bonds to form a solution of dibasic aromatic acid or ester, polyol, organic impurities, and other components of the resin; crystallization of the dibasic aromatic acid or ester from the solution by flash crystallization to form a vapor containing a major mount of the polyol and solvent, and a slurry of dibasic aromatic acid or ester crystals in mother liquor; separation of crude dibasic aromatic acid or ester from the mother liquor; crystallization of retained organic impurities from the mother liquor solution by flash crystallization to a pressure in a range downward from about one atmosphere to form a slurry of mother liquor solids; recovery of mother liquor solids from the slurry; and recycle of the recovered mother liquor solids to the depolymerization.

20 Claims, 1 Drawing Sheet

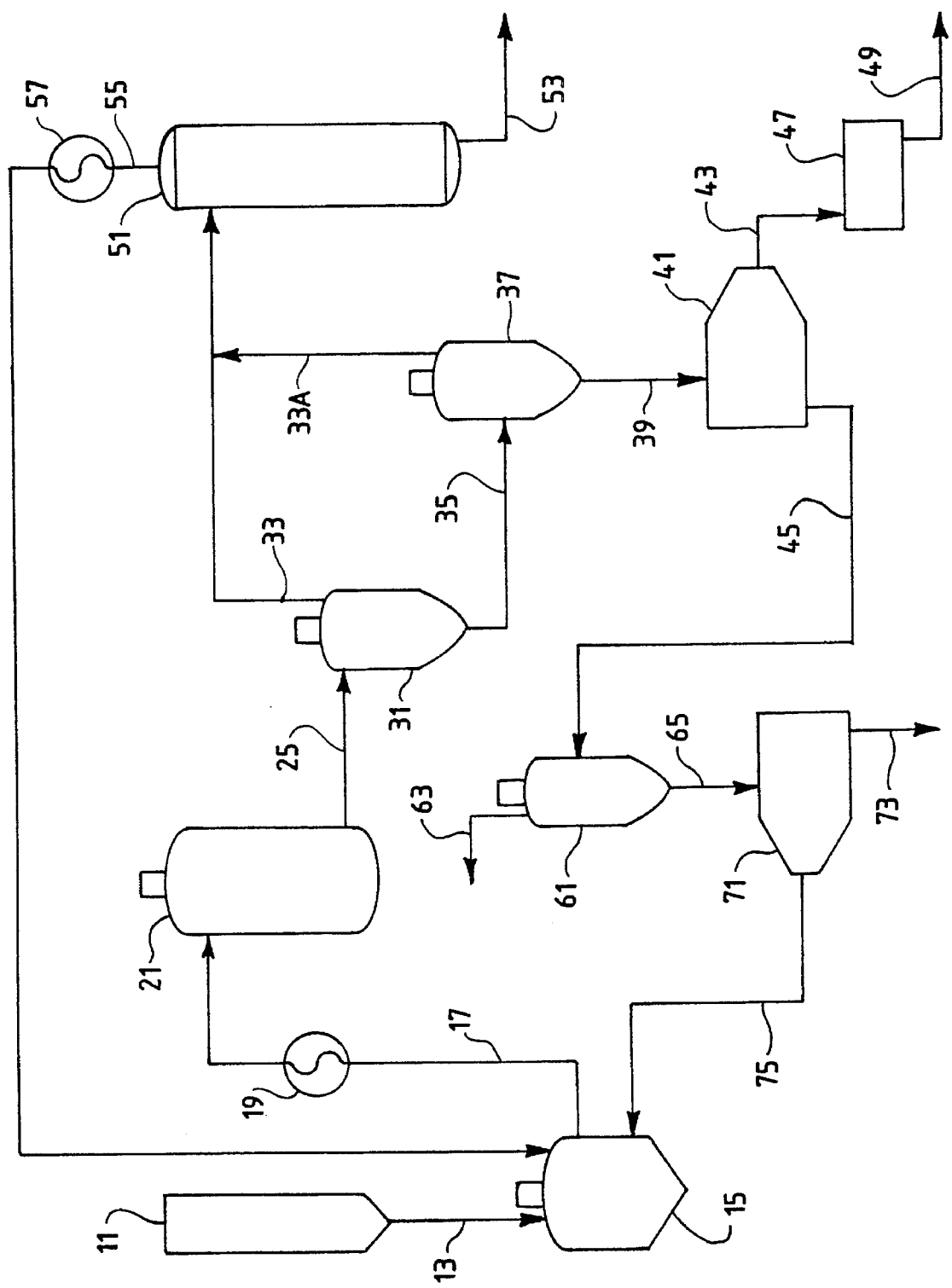

PROCESS FOR RECOVERY OF AROMATIC ACID OR ESTER AND POLYOL FROM WASTE POLYESTER RESINS

FIELD OF THE INVENTION

The field of this invention relates to preparation of polymerizable monomers from waste polyester resins having repeating units of aromatic acid residue and repeating units of polyol residue linked by ester bonds. More particularly, this invention concerns recovery processes involving liquid phase hydrolysis and/or alkanolysis of the ester bonds in a depolymerization zone, crystallization and separation of crystalline dibasic aromatic acid or its ester from mother liquor, crystallization and recovery of mother liquor solids from mother liquor, which solids are, advantageously, recycled to the depolymerization. Where the recovery of crystalline dibasic aromatic acid or its ester is by means of a flash crystallization system, vapor from the flash crystallization is fractionated to obtain polyol free of solvent, and a solvent fractionation which is, also advantageously, recycled to the depolymerization. Recovered polyol and crystals of dibasic aromatic acid or its ester are substantially free of more soluble impurities including many colored and color causing compounds, which are, typically, found in post-consumer polyester resins.

Several aspects of this invention relate to processes for manufacture of terephthalic acid which include depolymerizing polyethylene terephthalate resin to obtain a solution containing ethylene glycol, terephthalic acid, and intermediate products from the hydrolysis of waste polyethylene terephthalate resin, such as mono(2-hydroxyethyl)terephthalate (MHET). Processes, for example, in which dehydrated ethylene glycol product is recovered by an initial partial or total condensation of flash vapors and fractionation, terephthalic acid free of intermediate products from the hydrolysis is purified by hydrogenation, and/or mother liquor solids containing a major amount of intermediate product mono(2-hydroxyethyl)terephthalate are recycled to the depolymerization.

In another aspect this invention relates to processes for manufacture of 2,6-naphthalene dicarboxylic acid or an ester thereof which processes include both recovering 2,5-naphthalene dicarboxylic acid or its ester and dihydric alcohol. Waste poly(ethylene-2,6-naphthalate) resins are, according to this invention, depolymerized by hydrolysis or methanolysis to obtain a mixture containing ethylene glycol, 2,6-naphthalene dicarboxylic acid or its dimethyl ester, and volatile products from the depolymerization of waste poly(ethylene-2,6-naphthalate) resin.

BACKGROUND OF THE INVENTION

Aromatic dicarboxylic acids are well known starting materials for making polyester resins, which polyester resins are used widely as principal polymers for polyester fibers, polyester films, and resins for bottles and like containers. For a polyester resin to have properties required in many of these uses, the polyester resin must be made from a polymer grade or "purified" aromatic acid, such as purified terephthalic acid.

Purified terephthalic acid is derived from relatively less pure, technical grade or "crude" terephthalic acid by purification of the latter utilizing hydrogen and a noble metal catalysts as described in U.S. Pat. No. 3,584,039 to Meyer. In the purification process, impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts various color bodies present in the relatively impure terephthalic acid to colorless products. Another related purification-by-hydrogenation process of aromatic polycarboxylic acids produced by liquid phase catalyst oxidation of polyalkyl aromatic hydrocarbons is described in U.S. Pat. No. 4,405,809 to Stech et al.

Depolymerization of polyethylene terephthalate by hydrolysis at a high temperature and pressure in the absence of a base or acid, or a catalyst, is known, see for example, U.S. Pat. No. 4,521,556; U.S. Pat. No. 4,578,502; U.S. Pat. No. 4,578,510; U.S. Pat. No. 4,605,762; GB. Patent No 2,123,403; U.S. Pat. No. 4,620,032; U.S. Pat. No. 4,626,598; Japanese Patent No. 49020147; and Japanese Patent No. 56118420. Depolymerization of polyethylene terephthalate by hydrolysis under conditions of neutral pH can, however, result in production of oligomeric co-products (U.S. Pat. No. 4,578,510); derivatives of terephthalic acid (Wolkma Chem., 13(2), 144–55); and/or cyclic trimers (Japanese Patent No. 56118420). Additionally, depolymerization product of waste polyethylene terephthalate in the form of bottles, film, fiber and other manufactured articles usually contain dyes and contaminants (U.S. Pat. No. 4,521,556; GB. Patent No 2,123,403; and Japanese Patent No. 49020147). Accordingly, although various processes are available for hydrolyzing polyethylene terephthalate waste, the purification of recovered terephthalic acid typically requires several process steps to remove dyes, pigments, and other impurities including inorganic compounds such as catalyst residues and organic compounds which can result from depolymerization reactions.

U.S. Pat. No. 4,355,175, to Pusztaszeri, exemplifies some difficulties encountered in preparing a purified terephthalic acid from polyethylene terephthalate waste. Polyester scrap such as film (with or without silver), fabric, yarn, or bottles, was depolymerized at ambient temperatures with a mixture of concentrated sulfuric acid and water to form crude terephthalic acid. Pusztaszeri states that an alkaline solution, which can be dark brown or black in color, containing crude terephthalic acid resulting from the depolymerization, is filtered to obtain a clear liquid which many be light brown in color (if colored, it must be treated with activated charcoal and filtered from the charcoal). The resulting solution is then acidified with sulfuric acid to precipitate the terephthalic acid. Terephthalic acid is then recovered by filtration and washed.

U.S. Pat. No. 4,578,502, to Cudmore, exemplifies a low yielding polyethylene terephthalate saponification process. Solid polyethylene terephthalate scrap is said to be reprocessed to form polymeric polyethylene terephthalate by depolymerizing the scrap in the presence of water or methanol, recovering monomers resulting from the depolymerization, and repolymerizing the monomers. Substantial amounts of "make-up" or fresh ethylene glycol appear to be required because of large losses of this monomer from the flash crystallizer. Soluble organic compounds which are less volatile than ethylene glycol, both impurities and recyclable products of depolymerization, are purged from this process as waste. Cudmore states that, when total depolymerization solution containing crude terephthalic acid resulting from the depolymerization is treated with activated charcoal, the precipitated terephthalic acid has a purity suitable for repolymerization. No working example is, however, reported.

In U.S. Pat. No. 5,051,528 to Naujokas and Ryan, a method is described for recovering ethylene glycol and forming dimethyl terephthalate from polyethylene terephthalate waste by dissolving the scrap in a solvent consisting of oligomers of the same monomers at atmospheric pressure and passing super-heated methanol through the solution at temperatures below 270° C. Dimethyl terephthalate and ethylene glycol are said to be carried out of the solution with the flow of super-heated methanol. Methanol is recovered overhead from the product vapor stream in a first distillation column. In a subsequent distillation column, dimethyl terephthalate and ethylene glycol are separated from a bottom effluent of the first distillation column. However, aromatic carboxylic acids cannot be obtained directly by this method because of the use of super-heated methanol resulting in formation of dimethyl terephthalate.

In a later filed European Patent Application No 484 963 A 2, in the name of Everette, a method is described for obtaining ethylene glycol vapor and forming dimethyl terephthalate vapor by treating polyester polymer with excess methanol vapors at a temperature above 230° C. The excess methanol is said to act as a carrier gas for the ethylene glycol vapor and dimethyl terephthalate vapor. At a pressure of 110 psig the reported yields of dimethyl terephthalate were, even with an excess of at least 3 moles of methanol for every mole of dimethyl terephthalate in the vapor, in a range downward from 88 mole percent based on PET content of the starting material. At lower pressures, lower yields were reported for this process. Again, aromatic carboxylic acids cannot be obtained directly by this method because of the use of excess methanol resulting in formation of dimethyl terephthalate.

Recently, in U.S. Pat. No. 5,095,145, to Rosen, a process is disclosed for preparing a purified terephthalic acid from waste polyethylene terephthalate. Scrap was depolymerized at temperatures of from about 221° C. to about 316° C. with water at pressures sufficient to maintain a liquid phase and, subsequent to cooling, a crude terephthalic acid filter cake was recovered from the resulting solution and washed. The cake was reslurried and dissolved in water. Thereupon, the solution obtained was catalytically hydrogenated at temperatures of from about 221° C. to about 316° C. at pressures sufficient to maintain a liquid phase for a period of up to 8 hours. Rosen states that pellets of green waste polyethylene terephthalate from waste green bottles were depolymerized by this process at 274° C. and samples of crude terephthalic acid filter cakes taken after 2 hours and a longer period. After filter cakes of terephthalic acid from green bottles were analyzed for color, L*-values of 91.54 and 68.18, a*-values of −0.55 and 1.22, and b*-values of 5.22 and 15.88, respectively, were reported. In Example XII of U.S. Pat. No. 5,095,145 it is stated that hydrogenation of crude terephthalic acid from waste green polyethylene terephthalate required up to about 6 hours to reduce initial b*-values greater than 2 but less than 10 to less than 2. The reported L*-value, however, increased to over 95 and a*-values also increased, but remained negative.

Regardless of the methods of depolymerization and purification of resulting terephthalic acid, the variable nature of crude terephthalic acid obtained from depolymerization of polyethylene terephthalate waste from many sources and the variable nature of impurities resulting therefrom and contained in the crude terephthalic acid, the process control and thus quality assurance of the purified terephthalic acid, has been made difficult and costly. Because of this lack of quality assurance and its cost relative to that of virgin purified terephthalic acid, purified terephthalic acid from polyethylene terephthalate waste has not been considered as a viable economic replacement for fiber grade virgin purified terephthalic acid prepared from para-xylene.

It is therefore a general object of the present invention to provide an improved method which overcomes the aforesaid problem of prior art methods, for recovery of aromatic acid from polyester resin which has been used for polyester fibers, polyester films, and resins in bottles and like containers.

More particularly, it is an object of the present invention to provide an improved method for recovery from polyester resins aromatic acid sufficiently free of undesired impurities so that the acid can be used to make polyester resins which have good color and other properties needed in manufacture of commercial articles.

Other objects and advantages of the invention will become apparent upon reading the following detailed description and appended claims.

SUMMARY OF THE INVENTION

Economical processes are disclosed for recovering dibasic aromatic acid or ester thereof, and polyol from polyester resin comprising repeating units of dibasic aromatic acid residue and repeating units of polyol residue linked by ester bonds. Generally, waste polyester resins comprise polyol residue derived from a dihydric alcohol, preferably a lower alkylene diol such as ethylene glycol. Processes according to this invention include, broadly, liquid phase hydrolysis and/or alkanolysis of the ester bonds in a depolymerization zone, flash crystallization and separation of crystalline dibasic aromatic acid or its ester from mother liquor, crystallization and recovery of mother liquor solids from mother liquor which solids are recycled to the depolymerization zone. Vapor from the flash crystallization is fractionated to obtain dihydric alcohol free of solvent, and a solvent fractionation which is, advantageously, recycled to the depolymerization.

More particularly, recovery processes according to this invention comprise: depolymerizing polyester resin in a liquid solvent, preferably comprising at least one member selected from the group consisting of water and methanol under conditions of elevated temperature and pressure suitable for opening of ester bonds to form a mixture comprising a solution of dibasic aromatic acid or an ester thereof, dihydric alcohol, organic impurities, and other components of the resin; crystallizing substantially all of the dibasic aromatic acid or ester from the solution by flash crystallization down to pressures of about one atmosphere to form a vapor containing a major amount of the dihydric alcohol and solvent, and a slurry of dibasic aromatic acid or ester crystals in mother liquor; separating from the mother liquor a product of crude dibasic aromatic acid or ester substantially free of dihydric alcohol, but containing some organic impurities; crystallizing retained organic impurities from the mother liquor solution by flash crystallization to pressures in a range downward from about one atmosphere to form a slurry of mother liquor solids; recovering mother liquor solids from the slurry; and recycling the recovered solids to the depolymerization mixture.

Typically, commercial polyester resin comprises repeating units of ethylene glycol residue. Waste polyester resin comprising repeating units derived from at least one member of the group consisting of isophthalic acid, terephthalic acid, and 2,6-naphthalene dicarboxylic acid are particularly useful in recovery processes according to this invention.

In one aspect of this invention, terephthalic acid or dimethyl terephthalate is produced from polyester resin comprising repeating units of terephthalic acid residue and repeating units of dihydric alcohol residue linked by ester bonds by a process which comprises: depolymerizing polyester resin in a liquid solvent under conditions of elevated temperature and pressure suitable for opening of ester bonds to form a mixture comprising a solution of terephthalic acid or dimethyl terephthalate, dihydric alcohol, organic impurities, and other products of the depolymerization; crystallizing substantially all of the terephthalic acid or dimethyl terephthalate from the solution by flash crystallization down to a pressure of about one atmosphere to form a vapor containing a major mount of the dihydric alcohol and lower boiling solvent, and a slurry of terephthalic acid or dimethyl terephthalate crystals in mother liquor; fractionating the flash vapor to obtain a liquid solvent fraction and a product fraction of dihydric alcohol substantially free of solvent, and recycling the recovered solvent to the depolymerization mixture; separating from the mother liquor a product of crude terephthalic acid or dimethyl terephthalate substantially free of dihydric alcohol, but containing some organic impurities; crystallizing retained organic impurities from the mother liquor solution by flash crystallization to a pressure in a range downward from about one atmosphere to about 1 psia to form a slurry of mother liquor solids; and recovering mother liquor solids from the slurry, and recycling the recovered solids to the depolymerization mixture.

In another aspect of this invention, terephthalic acid and ethylene glycol are produced from polyester resin comprising repeating units of terephthalic acid residue and repeating units of ethylene glycol residue linked by ester bonds by a process which comprises: depolymerizing polyethylene terephthalate resin in aqueous solvent under conditions of elevated temperatures in a range of from about 220° C. to about 400° C. and pressure sufficient to maintain a liquid phase suitable for hydrolysis of ester bonds to form a mixture comprising a solution of terephthalic acid, ethylene glycol, impurities comprising mono(2-hydroxyethyl)terephthalate, bis(2-hydroxyethyl)terephthalate, and other organic products of hydrolysis; crystallizing substantially all of the terephthalic acid from the solution by flash crystallization in two or more stages down to temperatures in a range from about 200° C. to about 70° C. to form a vapor containing a major mount of the ethylene glycol and water, and a slurry of terephthalic acid crystals in mother liquor; fractionating the flash vapor to obtain a water fraction and a product fraction of dehydrated ethylene glycol; recycling the recovered water fraction to the depolymerization mixture; separating from the mother liquor a product of crude terephthalic acid containing some organic impurities, but substantially free of ethylene glycol, mono(2-hydroxyethyl)terephthalate, and bis( 2-hydroxyethyl)terephthalate; crystallizing retained organic impurities from the mother liquor solution by flash crystallization to temperatures in a range downward from about 60° C. to form a slurry of mother liquor solids containing substantially all the mono(2-hydroxyethyl)terephthalate, and bis( 2-hydroxyethyl)terephthalate; recovering mother liquor solids from the slurry; and recycling the recovered mother liquor solids to the depolymerization mixture.

In several preferred embodiments processes for recovery of terephthalic acid according to this invention further comprise: reducing at least a portion of the organic impurities in the crude terephthalic acid in an aqueous solution at elevated temperatures and pressures and in the presence of hydrogen and an insoluble catalyst comprising at least one metal selected from the group consisting of palladium and rhodium; separating the solid metal-containing catalyst from the aqueous solution; and crystallizing and separating from the aqueous solution purified terephthalic acid having a total metals content of less than 100 ppm and containing less than 1000 ppm total of 4-carboxy-benzaldehyde and toluic acid.

Where desired, a dehydrated dihydric alcohol product is recovered by fractional distillation of effluent of the separation of solid aromatic acid product. At least a portion of the water vapor and/or the lower boiling compounds from the fractional distillation are, advantageously, recycled to the depolymerization.

Sources of waste polyester resins made from different aromatic acids are suitable, even without initial sorting. Processes according to this invention are particularly suitable for recovery of at least one member of the group consisting of isophthalic acid, terephthalic acid, and 2,6-naphthalene dicarboxylic acid. Polyethylene terephthalate and poly(ethylene-2,6-naphthalate) resins are, preferably, treated with excess water and/or a lower alkanol such as methanol at temperatures above about 150° C., preferably, temperatures are in a range of from about 200° C. to about 400° C. and at pressures sufficient to maintain a liquid phase. Generally, pressures in the depolymerization zones are below about 200 atmospheres, typically, pressures are in a range upward from about 10 atmosphere to about 150 atmospheres, and advantageously, pressures are in a range upward from about 25 atmosphere to about 150 atmospheres.

Where alcohol product of higher purity is desired, a process for recovering dihydric alcohol according to this invention, further comprises: fractionating at least a portion of vapors resulting from the flash crystallization of aromatic acid or ester from the products of depolymerization to obtain a dihydric alcohol product substantially free of lower boiling compounds. Generally, fractionation of the residue containing the desired alcohol is by means of continuous distillation to obtain an overhead fraction of lower boiling compounds, such as water, a dehydrated alcohol product, and a bottom fraction containing lower boiling compounds. At least a portion of the bottom fraction is, advantageously, recycled to one or more of the reaction zones where the depolymerization of polyester resin is carried out in the presence of the lower boiling compounds.

Where aromatic acid product of higher purity is desired, processes for recovering dibasic aromatic acid from polyester resin according to this invention, further comprises: reducing at least a portion of the organic impurities in the crude dibasic aromatic acid in an aqueous solution at elevated temperatures and pressures and in the presence of hydrogen and at least one insoluble Group VIII noble metal-containing catalyst; separating the solid noble metal-containing catalyst from the aqueous solution; and crystallizing and separating purified dibasic aromatic acid from the aqueous solution while maintaining the temperature in a range of from about 50° C. to about 150° C. The resulting purified terephthalic acid has a L*-value in a range of from about 95 to about 100, an a*-value in a range of from about −1 to about +1, and a b*-value in a range of from about 0.5 to about 2.

Fiber-grade terephthalic acid is, generally, obtained using a hydrogenation catalyst in which the noble metal is at least one member of the group consisting of palladium and rhodium. Purified terephthalic acid produced from waste polyethylene terephthalate according to this invention has a total metals content of less than about 400 ppm and, preferably, less than 100 ppm.

When the insoluble metal-containing catalyst has a palladium containing component on a carbon support, terephthalic acid produced from waste polyethylene terephthalate according to this invention has a total metals content of less than 10 ppm, and color measured by a L*-value greater than about 95, preferably in a range of from about 95 to about 100, an a*-value greater than about −1.5, preferably in a range of from about −1 to about +1, and a b*-value less than about 2, preferably in a range of from about 0.5 to about 2.

Processes for recovering terephthalic acid from polyethylene terephthalate resin, optionally, further comprise: reducing at least a portion of the organic impurities in the crude terephthalic acid in an aqueous solution at elevated temperatures and pressures and in the presence of hydrogen and an insoluble catalyst containing a palladium component on a carbon support; separating the insoluble catalyst from the aqueous solution; and crystallizing and separating purified terephthalic acid from the aqueous solution while maintaining the temperature in a range of from about 50° C. to about 150° C. Advantageously, resulting purified terephthalic acid has a L*-value in a range of from about 95 to about 100, an a*-value in a range of from about −1 to about +1, and a b*-value in a range of from about 0.5 to about 2.

Preferred processes for obtaining purified 2,6-naphthalene dicarboxylic acid further comprises: reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst; separating the solid noble metal-containing catalyst from the aqueous solution; and crystallizing and separating from the aqueous solution purified 2,6-naphthalene dicarboxylic acid while maintaining the temperature in a range of from about 25° C. to about 250° C. Advantageously, purified 2,6-naphthalene dicarboxylic acid has an optical density in a range from about 0 to about 5, an ash content of less 500 ppm, and/or a metals content of less than 200 ppm.

BRIEF DESCRIPTION OF THE INVENTION

Suitable sources of polyester resin for use in this invention include polyester fibers, polyester films, and manufactured articles such as bottles and like containers. Resins are, generally, made up of structural units which are repeated many times to obtain high molecular weight and other desired properties. In polyester resins repeating structural units are made up of dibasic acid residue and, typically, dihydric alcohol residue linked by ester bonds, i.e., units in which acidic hydrogen atoms of a dicarboxylic acid molecule are replaced by a hydrocarbon group. In preferred polyester resin for use in this invention, the repeating structural units are, generally, made up of aromatic acid residue, preferably, from aromatic acids. Carboxyl groups in preferred aromatic acids are either attached directly to an independent benzene ring or to benzene rings of a condensed ring system such as naphthalene, in which two benzene rings have two carbon atoms in common or anthracene in which three rings are similarly connected so that the tings are not independent.

Suitable polyester resins for use in methods producing aromatic acid according to this invention have repeating structural units containing residues of any dicarboxylic acid which can be formed from a corresponding methyl substituted aromatic compound by liquid-phase oxidation with an oxygen-containing gas in the presence of an oxidation catalyst at elevated pressures and temperatures. Polyester resins, for example, which have repeating structural units containing residues of isophthalic acid, terephthalic acid, naphthalene dicarboxylic acid, 4,4'-oxybis(benzoic acid), 5-tert-butyl-1,3-benzene dicarboxylic acid and the like. Particularly useful are polyester resins which have repeating structural units containing residues of terephthalic acid or 2,6-naphthalene dicarboxylic acid.

An essential element of processes according to this invention is that at least a portion of the organic impurities or intermediate co-products present in the depolymerization mixture and which are retained in mother liquor upon its separation from crystals of crude product, are recovered as solids from the mother liquor and recycled to the depolymerization mixtures. Thus, instant processes involve fewer problems in safely disposing of process wastes by other means, which can be costly, and yields of desired products are increased.

Processes according to this invention are advantageous in that the recovered aromatic acid and dihydric alcohol are freed of many components and impurities present in commercially available sources of post-consumer wastes. Thus, the make up of polyester waste is not critical to the recovery process and the inventive method is very satisfactory. Suitable sources of polyester include, for example, flaked and/or ground polyester bottles along with all their components, such as, polyethylene bottom cups; labels, bottle caps, and bottle contents; photographic and other sources of film scrap, and scrap containing other polymers including acetate resins, polyvinyl chloride and the like. Processes according to this invention are well suited to process wastes containing blends of polyester fibers with other fibers, such as cotton, polyester that is metallized, polyester that is dyed, polyester that is pigmented, and/or polyester that is mixed with other plastics.

Processes according to this invention are particularly useful in recovery of aromatic acid from polyester waste containing metallo-organic components used to color polyester articles, because of the excellent color obtained in polyesters made from the recovered aromatic acid. Copper containing components of polyester waste, for example, copper phthalocyanine ($C_{32}H_{16}CuN_8$) and compounds derived therefrom, cause impurities which are difficult to remove from aromatic acid. Copper levels in aromatic acid produced by processes of this invention are less than 5 ppm, and preferably less than 1 ppm.

In preparation of comminuted polyester resin, polyethylene terephthalate waste is, for example, subjected to the action of a granulator, or a crusher, or a grinding machine to reduce the waste material to a suitable particle size which can be as large as about one-half inch, or about 2 cm, in maximum length and about one-eight inch, or about 0.5 cm, in thickness.

During depolymerization particles of polyester resin are slurried with liquid solvent at any suitable concentration, typically, in a range of from about 10 weight percent to about 40 weight percent of solids, and preferably in a range of from about 20 weight percent to about 30 weight percent of solids. Generally, only a portion of the liquid solvent suitable to slurry the comminuted polyester participates in depolymerization reactions. Amount of solvent can be, advantageously, adjusted to facilitate the desired stages of flash crystallization. It is preferred that effluent of the depolymerization contain at least about 4 moles of solvent per mole of aromatic acid, and mole ratios as high as 150 moles of water per mole of aromatic acid are useful.

The purification step of the instant invention can be carried out in a batch mode as well as a continuous mode. For commercial scale purification of terephthalic acid a continuous mode is preferred. In any event, however, a*-value and b*-value of crude terephthalic acid and purified terephthalic acid are monitored so as to obtain a desired color level of final product, a fiber-grade terephthalic acid.

Terephthalic acid concentration in the solution to be purified by hydrogenation can vary over a relatively wide range. Concentration can be as low as about 5 percent by weight or as high as about 35 percent by weight, based on the weight of the solution. Preferably, the solution concentration of terephthalic acid is in a range of from about 10 to about 30 percent by weight.

Pressure employed in the purification step depends primarily upon the temperature employed therein. Inasmuch as the temperatures at which practical amounts of the impure terephthalic acid may be dissolved in an aforesaid solvent are substantially above the normal boiling point of the solvent, the process pressures are necessarily considerably above atmospheric pressure to maintain the aqueous solution in a liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. Use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in a range of about 200 to about 1,500 pounds per square inch gauge (psig), and usually is in a range of about 900 psig to about 1,200 psig.

The reactor employed in the purification step can be operated in several modes. For example, a predetermined liquid level can be maintained in the reactor, and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative mounts of hydrogen and inert gas present in the admixture.

In yet another operating mode, the reactor can be filled with the terephthalic acid solution so as to provide no reactor vapor space, that is, the reactor can be operated as a hydraulically full system with dissolved hydrogen being fed to the reactor under flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in a range of from about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

In general, the amount of hydrogen supplied to the purification reactor under reaction conditions is, of course, sufficient to effect the desired hydrogenation.

As described in the aforementioned U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one member of the group consisting of palladium and rhodium. Other catalysts effective for aqueous liquid-phase hydrogenation under the relatively mild hydrogenation conditions described herein above are listed in Kirk-Othmer, *Encyclopedia of Chemical Technology,* Wiley-Interscience, particularly in chapters on Hydrogenation and Catalysts. See also U.S. Pat. No. 2,070,770 to Amend and U.S. Pat. No. 2,105,664 to Lazier.

A preferred method for hydrogenation of crude 2,6-naphthalene dicarboxylic acid according to the present invention is the subject of U.S. Pat. No. 5,256,817 to Sikkenga and Hoover, the disclosure of which is incorporated herein by reference.

Preferably, the catalyst comprises a support. Preferred support materials include carbon and charcoal. Typically, the catalyst carrier is active carbon, usually that derived from coconut charcoal in the form of granules having a surface area of at least about 600 $m^2/g$ measured by the BET method using nitrogen. Other porous carbonaceous supports or substrates can, however, be used as long as the surface area requirements can be met. In addition to coconut charcoal, activated carbon derived from other plant or from animal sources can be utilized.

The noble metal component is present on the carrier at a concentration level in a range of from about 0.01 weight percent to about 2 weight percent, based on total weight of catalyst, i.e., metal plus active carbon carrier, and calculated as the elemental noble metal. Preferably, the catalyst metal loading is about 0.5 weight percent.

A typical catalyst of palladium on a support comprises from about 0.01 weight percent to about 2 weight percent of palladium, based on total weight of catalyst and calculated as elemental metal. The support or carrier for the palladium is porous and inert, and preferably is active carbon having a surface area of about 600 $m^2/g$ to about 1,500 $m^2/g$. Suitable supports for Pd/C hydrogenation catalysts are well-known and are described, inter alai, in U.S. Pat. No. 3,584,039 to Meyer.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (carbon Code CG-5)" and "Rhodium on Activated Carbon Granules (carbon Code CG-21)." Both of these catalysts have a BET; $N_2$ surface area of about 1,000 $m^2/g$ and have a particle size of 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Stem Activated Carbon Granules, Anhydrous."

Space velocity reported as weight of crude terephthalic acid solution per weight of catalyst per hour in the purification step is in a range of from about 5 hours$^{-1}$ to about 25 hours$^{-1}$, preferably from about 10 hours$^{-1}$ to about 15 hours$^{-1}$. Residence time of the solution in the catalyst bed varies, depending upon activity of catalysts present.

The color level of crude terephthalic acid, purified terephthalic acid product, and polyethylene terephthalate can be monitored or evaluated directly or indirectly, as described herein below. Partial pressure of hydrogen in the reactor can be adjusted to compensate for any detected impermissible deviation of the purified terephthalic acid from the desired color level. Adjustment can be made by the procedure taught in U.S. Pat. No. 4,782,181, which is incorporated herein by reference.

In one aspect, color level of crude terephthalic acid, purified terephthalic acid product, and polyethylene terephthalate can be ascertained by measuring its b*-value on the Hunter Color Scale as described in Hunter, The Measurement of Appearance, Chapter 8, pp. 103 to 132, John Wiley & Sons, N.Y. (1975), and in Wyszecki et al., Color Science Concepts and Methods, Quantitative Data and Formulae, 2d Ed., pp. 166 to 168, John Wiley & Sons, N.Y. (1982).

More specifically, b*-values of crude terephthalic acid, purified terephthalic acid product, and polyethylene terephthalate can be determined using, for example, a Diano Match Scan Spectrophotometer as follows. A sample of solid product is pressed into a pellet having a thickness of about 0.25 inch and a diameter of about 1 inch. The pellet is then irradiated with white light that has been UV-filtered. The spectrum of visible light reflected from the sample is determined and tristimulus values (X, Y, and Z) are computed using the CIE Standard Observer functions. Using a weighted-ordinate method, tristimulus values are obtained from the following equations:

$$X = \sum_{400}^{700} R\lambda\, x\lambda,\ Y = \sum_{400}^{700} R\lambda\, y\lambda,\ Z = \sum_{400}^{700} R\lambda\, z\lambda,$$

where $R\lambda$ is the percent reflectance of the pellet at wavelength $\lambda$ and $x\lambda$, $y\lambda$, and $z\lambda$ are Standard Observer functions at wavelength 1 for CIE Illuminated D65. Tristimulus values X, Y, and Z, identify the color of the pellet in terms of a mixture of primary colors that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100\, Y/Y_o)^{1/3} - 16$$

$$a^* = 500\, [(X/X_o)^{1/3} - (Y/Y_o)^{1/3}]$$

$$b^* = 500\, [(Y/Y_o)^{1/3} - (Z/Z_o)^{1/3}]$$

The L* value is a measure of the luminosity or whiteness of an object where a L* value of 100 is pure white, a L* value of 0 is black, and values in a range 0<L*<100 are gray. The L* value is strictly a function of tristimulus Y-value. The b*-value is a measure of a yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of purified terephthalic acid product can be correlated with optical density of (OD) of incoming feed and utilized to adjust the partial pressure of hydrogen in the reactor. Typically, optical density values can be determined using a spectrophotometer and a light beam having wavelength of 340 nanometers (nm) or millimicrons (mu), correlated with b*-value of purified terephthalic acid product at specific partial pressure of hydrogen for a given catalyst and then used to adjust the partial pressure of hydrogen during a particular process run so as to produce purified product having the desired b*-value.

It has been found that a 0.1 unit deviation in b*-value of purified terephthalic acid product can be compensated by an adjustment in partial pressure of hydrogen in the reactor of as low as about 5 psi to as high as about 60 psi depending upon activity of catalyst employed. If a fresh, relatively high activity catalyst is used, an initial adjustment in partial pressure of hydrogen required for a 0.1 unit deviation in b*-value is, usually, in a range of from about 5 psi to about 7.5 psi. As catalyst stabilizes, however, the adjustment in partial pressure of hydrogen required for a 0.1 unit deviation in b*-value is, usually, in a range of from about 40 psi to about 50 psi.

It has been found that a 0.1 unit change in optical density at 340 nm ($OD_{340}$) of feed solution correlates with about 0.05 unit change in b*-value of purified terephthalic acid product which is obtained from that particular feed solution. Thus, a 0.1 unit change in $OD_{340}$-value of the feed solution can, usually, be compensated by an adjustment in partial pressure of hydrogen in the reactor in a range of from about 2.5 psi to about 4 psi for a fresh, relatively high activity catalyst. As activity of a catalyst stabilizes during use, however, a 0.1 unit change in $OD_{340}$-value of the feed solution can, usually, be compensated by an adjustment in partial pressure of hydrogen in the reactor in a range of from about 20 psi to about 25 psi.

An overall relationship among b*-value, partial pressure of hydrogen in the reactor, and $OD_{340}$ can also be expressed as $$b^*\text{-value} \propto A(H_{2pp}) + C(OD_{340})$$

where $H_{2pp}$ designates partial pressure of hydrogen in the reactor expressed in psi, $OD_{340}$ is the optical density value of crude terephthalic acid feed solution of the reactor, A is a number in a range of from about 0.001 to about 0.03, and C is a number in a range of from about 0.4 to about 1.4.

Similarly, an overall relationship among b*-value, concentration of hydrogen in the reactor solution, and optical density at 340 nm can be expressed as $$b^*\text{-value} \propto D(H_{2conc.}) + C(OD_{340})$$

where $H_{2conc.}$ designates concentration of hydrogen in the reactor expressed in cubic centimeters of hydrogen at 1 atmosphere absolute pressure and 0° C. dissolved per gram of crude terephthalic acid feed solution, $OD_{340}$ is the optical density value of crude terephthalic acid feed solution of the reactor, D is a number in a range of from about 0.2 to about 5.75, and C is a number in a range of from about 0.4 to about 1.4.

If it is desired to modulate the concentration of hydrogen in the solution in a hydraulically full reactor directly by adjusting flow of gaseous hydrogen to the hydrogenation reactor, then in such an event hydrogen flow rate can be adjusted to provide a change in concentration of hydrogen in a range of from about 0.03 cc/g to about 0.3 cc/g for a 0.1 unit change in b*-value of the product to be implemented, or in a range of about 0.015 cc/g to about 0.15 cc/g for an observed 0.1 unit change in $OD_{340}$ of feed solution to the hydrogenation reactor.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Example 1

In this example purified terephthalic acid was recovered from a commercially available waste polyethylene terephthalate flake. About 50 weight percent of the water charged to the hydrolysis was recycled water from previous reactor runs with water recycle.

A 250 gallon (nominal) high-pressure reactor was manually loaded through a top charge port with commercially available waste polyethylene terephthalate flake from clear beverage bottles (200 lb), demineralized water (399 lb), and recycled water ( 0.91 weight percent ethylene glycol, 0.02 weight percent diethylene glycol, 0.45 weight percent acetaldehyde, 0.57 weight percent dioxane and balance water, 401 lb). The reactor was sealed. Typically, measurement of color level of crude terephthalic acid from this source of waste polyethylene terephthalate resin gave an a*-value of about −0.4 to about 0.9 (green), and a b*-value of about 5 to about 7 (yellow). During a period of 3.5 hours this reaction mixture was heated to temperatures in a range of about 240° C. to about 245° C. and held at temperature for 1 hour by circulating hot oil through a jacket surrounding the reactor sides and bottom. Reactor and contents were cooled evaporatively to temperatures in a range from about 100° C. to about 105° C. by depressurizing to ambient pressure. Total weight of condensed products removed overhead from the reactor during a 2 hour period of depressurization was 436 lb. The resulting slurry of crystals in mother liquor was discharged from the reactor into a conical insulated stainless steel drum. Solids were recovered from the total product by allowing the terephthalic acid crystals to settle for 10 minutes and then decanting off the hot mother liquor. Recovered terephthalic acid crystals (28 percent wetness) were dried in a batch tumble dryer as a single batch to less than 1.5 percent residual moisture. A sample of this crude terephthalic acid product (99.60% terephthalic acid, 0.36% MHET, and 0.04% BHET by L.C. analyses) was identified as Crude TA-1. Crude TA-1 (290 grams) was charged to a 1 gallon titanium autoclave as a 20 percent slurry in deionized water and batch hydrogenated for 2 hours at 280° C. in the presence of catalyst (0.5 wt % Pd on C). A solution recovered from the hydrogenation was cooled to 150° C and resulting terephthalic acid crystals were recovered by filtration. This cake was washed with an equal amount of deionized water, dried, identified as Purified TA-1. Analysis of Purified TA-1 found that it contained less than 10 ppm by weight of 4-CBA and less than 10 ppm by weight of p-toluic acid. Measurement of color level for Purified TA-1 gave a L*-value of 94.54, an a*-value of −0.01, and a b*-value of 1.05.

Example 2

The procedure of Example 1 was again followed in this example, except that wet mother liquor solids recovered from previous reactor runs were recycled to the hydrolysis and about 70 weight percent of the water charged to the hydrolysis was recycled water. Recycle solids, used in this example were obtained from mother liquor decanted from two previous reactor runs. Hot mother liquor was allowed to cool to ambient temperature (32° C.), to form a mother liquor slurry containing precipitated MHET crystals. Wet mother liquor solids were separated from the mother liquor slurry by centrifugation.

A 250 gallon (nominal) high-pressure reactor was manually loaded through a top charge port with commercially available waste polyethylene terephthalate flake (250 lb), demineralized water (300 lb), recycled water (436 lb), and wet mother liquor solids (62 lb, 24% total solids). The reactor was sealed. During a period of 3.5 hours this reaction mixture was heated to temperatures in a range of about 250° C. to about 260° C. and held at temperature for 1 hour by circulating hot oil through a jacket surrounding the reactor sides and bottom. Reactor and contents were cooled evaporatively to temperatures in a range from about 100° C. to about 105° C. by depressurizing to ambient pressure. Total weight of condensed products removed overhead from the reactor during a 2 hour period of depressurization was 430 lb. The resulting slurry of crystals in mother liquor was discharged from the reactor into a conical insulated stainless steel drum. Solids were recovered from the total product by allowing the terephthalic acid crystals to settle for 10 minutes and then decanting off the hot mother liquor. Recovered terephthalic acid crystals were dried in a batch tumble dryer as a single batch to less than 1.3 percent residual moisture. A sample of this crude terephthalic acid product (99.58% terephthalic acid, 0.36% MHET, and 0.06% BHET by L.C. analyses) was identified as Crude TA-2. Crude TA-2 (290 grams) was charged to a 1 gallon titanium autoclave as a 20 percent slurry in deionized water and batch hydrogenated for 2 hours at 280° C. in the presence of catalyst (0.5 wt % Pd on C). A solution recovered from the hydrogenation was cooled to 150° C. and resulting terephthalic acid crystals were recovered by filtration. This cake was washed with an equal mount of deionized water, dried, identified as Purified TA-2. Analysis of Purified TA-2 found that it contained less than 10 ppm by weight of 4-CBA and less than 10 ppm by weight of p-toluic acid. Measurement of color level for Purified TA-2 gave a L*-value of 39.57, an a*-value of 0.02, and a b*-value of 1.9.

Example 3

In this example purified terephthalic acid was recovered from a commercially available waste polyethylene terephthalate flake.

A 1 gallon (nominal) high-pressure reactor was manually loaded through a top charge port with commercially available waste polyethylene terephthalate flake from dear beverage bottles (400 grams), and demineralized water (1200 grams). The reactor was sealed. Typically, measurement of color level of crude terephthalic acid from this source of waste polyethylene terephthalate resin gave an a*-value of about −0.7 to about 0.9 (green), and a b*-value of about 5 to about 7 (yellow). This reaction mixture was heated to temperatures in a range of about 270° C. to about 285° C. and held at temperature for 1 hour. Reactor and contents were cooled to temperatures in a range from about 145° C. to about 155° C. Solids were recovered by filteration. Recovered terephthalic acid crystals (17 percent wetness) were dried to less than 1.5 percent residual moisture. A sample of this crude terephthalic acid product (299 grams, 99.3% terephthalic acid, 0.25% MHET by L.C. analyses) was identified as Crude TA-3.

Example 4

The procedure of Example 3 was again followed in this example, except that wet mother liquor solids recovered from previous reactor runs were recycled to the hydrolysis. Hot mother liquor was allowed to cool to ambient temperature (32° C.), to form a mother liquor slurry containing precipitated MHET crystals. Wet mother liquor solids were separated from the mother liquor slurry by filtration.

A 1 gallon (nominal) high-pressure reactor was manually loaded through a top charge port with commercially available waste polyethylene terephthalate flake (400 grams), demineralized water (1200 grams), and wet mother liquor solids (60 grams). The reactor was sealed. This reaction mixture was heated to temperatures in a range of about 270° C. to about 280° C. and held at temperature for 1 hour. Reactor and contents were cooled to temperatures in a range from about 145° C. to about 155° C. Recovered terephthalic acid crystals were dried as a single batch to less than 1.3 percent residual moisture. A sample of this crude terephthalic acid product (322 grams, 99.4% terephthalic acid by L.C. analyses) was identified as Crude TA-4.

Example 5

The procedure of Example 3 was again followed in this example, except that the sealed reactor was heated to temperatures in a range of about 275° C. to about 280° C. and held at temperature for 15 minutes. Crude terephthalic acid product (85% terephthalic acid, and 15% MHET) was identified as Crude TA-5.

Example 6

The procedure of Example 3 was again followed in this example, except that the sealed reactor was heated to temperatures in a range of about 230° C. to about 235° C. and held at temperature for 135 minutes. Crude terephthalic acid product (96% terephthalic acid, and 4% MHET) was identified as Crude TA-6.

BRIEF DESCRIPTION OF THE DRAWINGS

Accompanying FIG. 1, forming part of the specification, is a simplified diagrammatic representation of a portion of aft integrated commercial system for recovery of an aromatic dicarboxylic acid from waste polyester resin and includes provisions for hydrolysis of the ester bonds, introducing the materials essential for hydrolysis such as a slurry of polyester resin particles in water, for receiving effluent from the depolymerization, forming and separating from other products of depolymerization a vapor fraction containing dihydric alcohol and water, recovering crystals of the aromatic dicarboxylic acid from mother liquor, dehydrating the dihydric alcohol, and recovering crystals of recyclable products of depolymerization from mother liquor.

BRIEF DESCRIPTION OF PREFERRED EMBODIMENTS

While this invention is susceptible of embodiment in many different forms, this specification and accompanying drawings disclose only some specific forms as an example of the use of the invention. In particular preferred embodiments of the invention for recovery of terephthalic acid and ethylene glycol from impure, post-consumer polyethylene terephthalate are illustrated and described. The invention is not intended to be limited to the embodiments so described, and the scope of the invention will be pointed out in the appended claims.

The apparatus of this invention is used with certain conventional components the details of which, although not fully illustrated or described, will be apparent to those having skill in the art and an understanding of the necessary function of such components.

More specifically with reference to FIG. 1, the. integrated system comprises one or more hydrolysis vessels, such as hydrolysis vessel 21 shown without means for agitating the aqueous mixture containing polyethylene terephthalate resin in the hydrolysis zone. Mechanical and/or other means for agitating the liquid, such as a stirrer and/or recirculation system may, however, be desired or needed by the particular design of hydrolysis vessel 21 and the manner in which materials essential for hydrolysis are introduced into the hydrolysis zone. Theoretical water for hydrolysis of the ester bonds involved in completely depolymerizing polyethylene terephthalate resin is 2 moles per mole of terephthalic acid or ethylene glycol residue.

Operation of the system is started by transferring flaked or granulated waste resin from feed silo 11 by pneumatic and/or mechanical conveyor system 13 to feed slurry tank 15 where a transferable feed slurry is formed by mixing solid waste particles with water supplied to feed slurry tank 15 via conduit 55 and water purification system (not shown). Feed slurry is fed through preheater 19 and transfer conduit 17 discharging into the aqueous mixture containing polyethylene terephthalate resin into the hydrolysis zone of hydrolysis vessel 21. Hydrolysis vessel 21 is, advantageously, provided with means for adding external heat to the liquid pool and controlling temperatures in the hydrolysis zone.

Depolymerization of waste polyethylene terephthalate resins in aqueous solvent is, generally, carried out at temperatures in a range of from about 200° C. to about 400° C., preferably at temperatures in a range of from about 230° C. to about 350° C., and any suitable pressure at least sufficient to maintain a liquid aqueous phase in the hydrolysis zone, typically at pressures in a range of from about 395 psig to about 2350 psig.

An aqueous mixture containing ethylene glycol, terephthalic acid, and other products of hydrolysis is discharged from the hydrolysis zone of hydrolysis vessel 21 through transfer line 25 to a first flash crystallizer 31 which is operated at any suitable temperature in a range downward from about 200° C. An aqueous slurry containing crystals of terephthalic acid in the first flash crystallizer is discharged through transfer line 35 to a last flash crystallizer 37 which is operated at any suitable temperature in a range upward from about 70° C. While in this embodiment two stages of crystallization are used, three, four, or more stages of crystallization may, advantageously, be employed to obtain desired crystal properties.

Separation of the solid phase (crystallized terephthalic acid) from the liquid phase (a substantially aqueous mother liquor solution containing ethylene glycol, mono( 2-hydroxyethyl)terephthalate, and other soluble products of depolymerization) can be accomplished by the use of any device for accomplishing such a phase separation. For example, the phase separation can be carried out by decantation, filtration or centrifugation. Centrifugal filters, filter presses or vacuum rotary filters can be employed for recovering the crystallized terephthalic acid from the mother liquor. The slurry of terephthalic acid crystals having a solids content of from about 2 to about 50 weight percent solids, is withdrawn from the bottom of the last flash crystallizer 37 through conduit 39 discharging into solid-liquid separator 41 to obtain a terephthalic acid cake. Wet cake containing from about 10 to about 50 weight percent moisture, is discharged from separator 41 through transfer line 43 to acid product dryer 47. Transfer line 43 is preferably a screw conveyor although belt or scoop conveyors can also be used in this service. Vapor from product dryer 47 is fed to an overhead vent scrubber system (not shown) along with other such vent streams of this recovery process. Dry product is conveyed by conveyor 49 to silo storage (not shown).

Mixtures containing stem, ethylene glycol vapor, and other volatile products of hydrolysis, but substantially free of lower boiling intermediate products from the hydrolysis such as mono(2-hydroxyethyl)terephthalate, are discharged from the product crystallizers 31 and 37 through transfer conduits 33 and 33A, respectively, to dehydration tower 51 operated at near atmospheric pressures, typically at pressures in a range of from about 5 psig to about 50 psig. Ethylene glycol free of more volatile compounds is withdrawn from dehydration tower 51 as a bottom product through transfer conduit 53. Water vapor is taken overhead from dehydration tower 51 through cooler/condenser 57 and returned to the feed slurry tank 15 through conduit 55.

Mother liquor from separator 41 is transferred through conduit 45 to vacuum crystallizer 61 operated at temperatures in a range downward from about 60° C., preferably in a range from about 55° C. to 5° C., and more preferably below about 45° C. Vapors are withdrawn from vacuum crystallizer 61 by a vacuum system (not shown) through conduit 63. Other suitable means of cooling mother liquor in the crystallizer may be employed alone or in combination with this vacuum system to obtain the precipitant.

Separation of the solid phase (containing mono(2-hydroxyethyl)terephthalate crystals) from the liquid phase (a substantially aqueous mother liquor solution containing more soluble products of depolymerization) can be accomplished by the use of any device for accomplishing such a phase separation. A slurry of the precipitant having a solids content of from about 1 to about 15 weight percent solids, is withdrawn from the bottom of vacuum crystallizer 61 through conduit 65 discharging into solid-liquid separator 71 to obtain a cake containing mono(2-hydroxyethyl)terephthalate crystals. Wet cake containing from about 20 to about 60 weight percent moisture, is discharged from separator 71 and returned to the feed slurry tank 15 through transfer line 75. Transfer line 75 is preferably a screw conveyor although belt or scoop conveyors can also be used in this service.

That which is claimed is:

1. A process for recovering dibasic aromatic acid or an ester thereof from polyester resin comprising repeating units of dibasic aromatic acid residue and repeating units of dihydric alcohol residue linked by ester bonds which process comprises:

depolymerizing polyester resin in a liquid solvent under conditions of elevated temperature and pressure suitable for opening of ester bonds to form a mixture comprising a solution of dibasic aromatic acid or an ester thereof, dihydric alcohol, organic impurities, and other components of the resin;

crystallizing substantially all of the dibasic aromatic acid or ester from the solution by flash crystallization down to pressure of about one atmosphere to form a vapor containing a major mount of the dihydric alcohol and solvent, and a slurry of dibasic aromatic acid or ester crystals in mother liquor;

separating from the mother liquor a product of crude dibasic aromatic acid or ester substantially free of dihydric alcohol, but containing some organic impurities;

crystallizing retained organic impurities from the mother liquor solution by flash crystallization to a pressure in a range downward from about one atmosphere to form a slurry of mother liquor solids;

recovering mother liquor solids from the slurry; and recycling the recovered solids to the depolymerization mixture.

2. The process according to claim 1 wherein the polyester resin comprises repeating units of ethylene glycol residue.

3. The process according to claim 1 wherein the depolymerizing of polyester resin is carried out in liquid solvent comprising a lower alkanol under conditions suitable for alkanolysis of ester bonds to form corresponding ester of the dibasic aromatic add.

4. The process according to claim 3 wherein the polyester resin comprises repeating units of 2,6-naphthalene dicarboxylic acid residue, and the lower alkanol is methanol.

5. The process according to claim 3 wherein the polyester resin comprises repeating units of terephthalic acid residue, and the lower alkanol is methanol.

6. The process according to claim 1 wherein the depolymerizing of polyester resin is carried out in an aqueous solvent under conditions suitable for hydrolysis of ester bonds to form dibasic aromatic acid.

7. The process according to claim 6 wherein the polyester resin comprises repeating units of ethylene glycol residue.

8. The process according to claim 6 wherein the polyester resin comprises repeating units of 2,6-naphthalene dicarboxylic acid residue.

9. The process according to claim 6 wherein the process further comprises:

reducing at least a portion of the organic impurities in the crude dibasic aromatic acid in an aqueous solution at elevated temperatures and pressures and in the presence of hydrogen and at least one insoluble Group VIII noble metal-containing catalyst;

separating the solid noble metal-containing catalyst from the aqueous solution; and crystallizing and separating purified dibasic aromatic acid from the aqueous solution.

10. The process according to claim 9 wherein the polyester resin comprises repeating units of terephthalic acid residue, the noble metal is at least one member of the group consisting of palladium and rhodium, and the purified dibasic aromatic acid has a total metals content of less than 100 ppm and contains less than 1000 ppm total of 4-carboxybenzaldehyde and toluic acid.

11. A process for recovering terephthalic acid or dimethyl terephthalate from polyester resin comprising repeating units of terephthalic acid residue and repeating units of dihydric alcohol residue linked by ester bonds which process comprises:

depolymerizing polyester resin in a liquid solvent comprising at least one member of the group consisting of water and methanol under conditions of elevated temperature and pressure suitable for opening of ester bonds to form a mixture comprising a solution of terephthalic acid or dimethyl terephthalate, dihydric alcohol, organic impurities, and other products of the depolymerization;

crystallizing substantially all of the terephthalic acid or dimethyl terephthalate from the solution by flash crystallization down to a pressure of about one atmosphere to form a vapor containing a major amount of the dihydric alcohol and lower boiling solvent, and a slurry of terephthalic acid or dimethyl terephthalate crystals in mother liquor;

fractionating the flash vapor to obtain a liquid solvent fraction and a product fraction of dihydric alcohol substantially free of solvent, and recycling the recovered solvent to the depolymerization mixture;

separating from the mother liquor a product of crude terephthalic acid or dimethyl terephthalate substantially free of dihydric alcohol, but containing some organic impurities;

crystallizing retained organic impurities from the mother liquor solution by flash crystallization to pressure in a range downward from about one atmosphere to about 1 psia to form a slurry of mother liquor solids; and recovering mother liquor solids from the slurry, and recycling the recovered solids to the depolymerization mixture.

12. The process according to claim 11 wherein the polyester resin comprises repeating units of ethylene glycol residue.

13. The process according to claim 12 wherein the depolymerizing of polyester resin is carried out in an aqueous solvent at temperatures in a range of from about 220° C. to about 400° C. to form solution comprising terephthalic acid, ethylene glycol, organic impurities, and other products of the depolymerization.

14. The process according to claim 12 wherein the depolymerizing of polyester resin is carried out in an aqueous solvent, and the flash crystallization is carried out at temperatures in a range from about 200° C. to about 70° C. to form a vapor containing a major amount of the ethylene glycol and water, and a slurry of terephthalic acid crystals in mother liquor.

15. The process according to claim 12 wherein the depolymerizing of polyester resin. is carried out in an aqueous solvent, and the crystallization of retained organic impurities from the mother liquor solution is carried out at temperatures in a range downward from about 60° C.

16. The process according to claim 12 wherein the depolymerizing of polyester resin is carried out in liquid solvent comprising methanol at temperatures in a range of from about 80° C. to about 220° C. to form solution comprising dimethyl terephthalate, ethylene glycol, organic impurities, and other products of the depolymerization.

17. The process according to claim 16 wherein the flash crystallization is carried out at temperatures in a range from about 200° C. to about 50° C. to form a vapor containing a major amount of the ethylene glycol and methanol, and a slurry of dimethyl terephthalate crystals in mother liquor.

18. The process according to claim 17 wherein the crystallization of retained organic impurities from the mother liquor solution is carried out at temperatures in a range downward from about 40° C.

19. A process for recovering terephthalic acid from polyester resin comprising repeating units of terephthalic acid residue and repeating units of ethylene glycol residue linked by ester bonds which process comprises:

depolymerizing polyethylene terephthalate resin in aqueous solvent under conditions of elevated temperatures in a range of from about 220° C. to about 400° C. and pressure sufficient to maintain a liquid phase suitable for hydrolysis of ester bonds to form a mixture comprising a solution of terephthalic acid, ethylene glycol, impurities comprising mono(2-hydroxyethyl)terephthalate, bis(2-hydroxyethyl)terephthalate, and other organic products of hydrolysis;

crystallizing substantially all of the terephthalic acid from the solution by flash crystallization in two or more stages down to temperatures in a range from about 200° C. to about 70° C. to form a vapor containing a major mount of the ethylene glycol and water, and a slurry of terephthalic acid crystals in mother liquor;

fractionating the flash vapor to obtain a water fraction and a product fraction of dehydrated ethylene glycol;

recycling the recovered water fraction to the depolymerization mixture;

separating from the mother liquor a product of crude terephthalic acid containing some organic impurities, but substantially free of ethylene glycol, mono(2-hydroxyethyl)terephthalate, and bis(2-hydroxyethyl)terephthalate;

crystallizing retained organic impurities from the mother liquor solution by flash crystallization to temperatures in a range downward from about 60° C. to form a slurry of mother liquor solids containing substantially all the mono(2-hydroxyethyl)terephthalate, and bis(2-hydroxyethyl)terephthalate;

recovering mother liquor solids from the slurry; and recycling the recovered mother liquor solids to the depolymerization mixture.

20. The process according to claim 19 wherein the process further comprises:

reducing at least a portion of the organic impurities in the crude terephthalic acid in an aqueous solution at elevated temperatures and pressures and in the presence of hydrogen and an insoluble catalyst comprising at least one metal selected from the group consisting of palladium and rhodium;

separating the solid metal-containing catalyst from the aqueous solution; and crystallizing and separating from the aqueous solution purified terephthalic acid having a total metals content of less than 100 ppm and containing less than 1000 ppm total of 4-carboxy-benzaldehyde and toluic acid.

* * * * *

UNITED STATES PATENT AND TRADEMARK OFFICE
CERTIFICATE OF CORRECTION

PATENT NO.: 5,502,247

Page 1 of 2

DATED: March 26, 1996

INVENTOR(S): Thomas M. Bartos, Bruce I. Rosen, Jeffrey I. Rosenfeld

It is certified that error appears in the above-identified patent and that said Letters Patent is hereby corrected as shown below:

| Col. | Line | |
|---|---|---|
| | Title | page, item [57]: |
| | 19-20 | in the "ABSTRACT" patent reads "a vapor containing a major mount of the polyol and solvent," it should read --a vapor containing a major amount of the polyol and solvent,-- |
| 5 | 41-42 | "a vapor containing a major mount of the ethylene glycol and water," should read --a vapor containing a major amount of the ethylene glycol and water,-- |
| 7 | 57-58 | "three rings are similarly connected so that the tings are not independent." should read --three rings are similarly connected so that the rings are not independent.-- |
| 9 | 48 | "relative mounts of hydrogen" should read --relative amounts of hydrogen-- |
| 11 | 3-4 | "Stem Activated Carbon Granules," should read --Steam Activated Carbon Granules,-- |

UNITED STATES PATENT AND TRADEMARK OFFICE
CERTIFICATE OF CORRECTION

PATENT NO.: 5,502,247

DATED: March 26, 1996

INVENTOR(S): Thomas M. Bartos, Bruce I. Rosen, Jeffrey I. Rosenfeld

It is certified that error appears in the above-identified patent and that said Letters Patent is hereby corrected as shown below:

| Col. | Line | |
|---|---|---|
| 14 | 62-63 | "dear beverage bottles" should read --clear beverage bottles-- |
| 15 | 56-57 | "a portion of aft integrated commercial system" should read --a portion of an integrated commercial system-- |
| 17 | 21 | "Mixtures containing stem," should read --Mixtures containing steam,-- |
| 18 | 7 | "a major mount of the dihydric alcohol" should read --a major amount of the dihydric alcohol-- |
| 18 | 27 | "dibasic aromatic add." should read --dibasic aromatic acid.-- |
| 20 | 22-23 | "a major mount of the ethylene glycol and water," should read --a major amount of the ethylene glycol and water,-- |

Signed and Sealed this

Third Day of December, 1996

Attest:

BRUCE LEHMAN

Attesting Officer   Commissioner of Patents and Trademarks